United States Patent [19]
Maag et al.

[11] Patent Number: 5,750,343
[45] Date of Patent: May 12, 1998

[54] METHODS OF DETECTING NUCLEIC ACIDS WITH NUCLEOTIDE PROBES CONTAINING 4'-SUBSTITUTED NUCLEOTIDES AND KITS THEREFOR

[75] Inventors: Hans Maag, Menlo Park; Samuel J. Rose, Mountain View, both of Calif.; Beat Schmidt, Baltschieder, Switzerland

[73] Assignee: Syntex Inc., Palo Alto, Calif.

[21] Appl. No.: 433,855

[22] Filed: May 2, 1995

Related U.S. Application Data

[62] Division of Ser. No. 164,893, Dec. 9, 1993, Pat. No. 5,446,137.

[51] Int. Cl.[6] .............................. C07H 21/04; C12Q 1/68
[52] U.S. Cl. ........................ 435/6; 536/23.1; 536/24.3; 536/24.32; 536/25.3; 536/25.32
[58] Field of Search ........................... 435/6; 536/23.1, 536/24.3, 24.32, 25.3, 25.32

[56] References Cited

U.S. PATENT DOCUMENTS

| | | | |
|---|---|---|---|
| 4,247,544 | 1/1981 | Bergstrom et al. | 424/180 |
| 4,267,171 | 5/1981 | Bergstrom et al. | 424/180 |
| 4,707,440 | 11/1987 | Stavrianopoulos | 435/6 |
| 4,711,955 | 12/1987 | Ward et al. | 536/29 |
| 4,948,882 | 8/1990 | Ruth | 536/27 |
| 4,994,373 | 2/1991 | Stavrianopoulos et al. | 435/6 |
| 4,996,143 | 2/1991 | Heller et al. | 435/6 |
| 5,082,830 | 1/1992 | Brakel et al. | 514/44 |

FOREIGN PATENT DOCUMENTS

| | | |
|---|---|---|
| 0 123 300 A2 | 10/1984 | European Pat. Off. . |
| 0 302 175 A2 | 2/1989 | European Pat. Off. . |
| 0 457 326 A1 | 11/1991 | European Pat. Off. . |
| 0 479 640 A2 | 4/1992 | European Pat. Off. . |

OTHER PUBLICATIONS

O–Yang et al., Tetrahedron 33:37–40, 1992.
Dan et al., Bioorganic & Medicinal Chemistry Letters 3(4):615–618, 1993.
Englisch, et al., Angewandte Chemie Int. Ed. Engl., vol. 30(6) (1991), pp. 613–629 "Chemically Modified Oligonucleotides as Probes and Inhibitors".
Azhayev, et al., Tetrahedron Letters, vol. 34:40 (1993), pp. 6435–6438 "Analogues of Oligonucleotides Containing 3'–Deoxy–β–D–Psicothymidine".
Dan, et al., Bioorganic & Medicinal Chemistry Letters, vol. 3:4 (1993), pp. 615–618 "Nucleosides & Nucleotides, 118. Synthesis of Oligonucleotides Containing A Novel 2"–Deoxyuridine Analogue That Carries An Aminoalkyl Tether At 1'–Position; Stabilization Of Duplex Formation By an Intercalating Group Accommodated In The Minor Groove".
O–Yang, et al., Tetrahedron Letters, vol. 33:1 (1992), pp. 37–40 "Synthesis of 4'–Cyanothymidine and Analogs as Potent Inhibitors of HIV[1]".
Maag, et al., Journal of Medicinal Chemistry, vol. 35 (1992), pp. 1440–1451 "Synthesis and Anti–HIV Activity of 4'–Azido–and 4'–Methoxynucleosides".
Stein, et al., Science, vol. 261, (Aug. 20, 1993), pp. 1004–1012 "Antisense Oligonucleotides as Therapeutic Agents—Is the Bullet Really Magical?".
Hai, et al., J. Medical Chemistry, vol. 25 (1982), pp. 806–812 "Species or Isozyme–Specific Enzyme Inhibitors. Selective Effects in Inhibitions of Rat Adenylate Kinase Isozyme by Adenosine 5'–Phosphate".

*Primary Examiner*—W. Gary Jones
*Assistant Examiner*—Paul B. Tran
*Attorney, Agent, or Firm*—Pauline Ann Clarke; Theodore J. Leitereg

[57] ABSTRACT

This invention relates to use of oligonucleotides having at least one nucleotide that is substituted at the 4'-position of the sugar moiety with a substituent other than hydrogen as nucleotide probes in methods for detecting the presence or amount of a polynucleotide analyte in a sample suspected of containing the polynucleotide analyte. These oligonucleotides can also be packaged in diagnostic assay kits.

23 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Synthetic ( x i ) SEQUENCE DESCRIPTION: SEQ ID NO:1:

GTTCGCCTAC GTGGCCTTTG                                                          20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Synthetic ( x i ) SEQUENCE DESCRIPTION: SEQ ID NO:2:

GTTCGCCTAC GTGGCCTTTG                                                          20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Synthetic ( x i ) SEQUENCE DESCRIPTION: SEQ ID NO:3:

GTTCGCCTAC GTGGCCTTTG 20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Synthetic ( x i ) SEQUENCE DESCRIPTION: SEQ ID NO:4:

GTTCGCCTAC GTGGCCTTTG 20

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Synthetic ( x i ) SEQUENCE DESCRIPTION: SEQ ID NO:5:

CAAGCGGATG CACCGGAAAC 20

METHODS OF DETECTING NUCLEIC ACIDS WITH NUCLEOTIDE PROBES CONTAINING 4'-SUBSTITUTED NUCLEOTIDES AND KITS THEREFOR

This application is a Division of application Ser. No. 08/164,893, filed Dec. 9, 1993, now U.S. Pat. No. 5,446,137.

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid or ribonucleic acid to form a hydrogen bonded structure with a complementary nucleic acid sequence has been employed as an analytical tool in molecular biology research and recombinant DNA technology.

Commonly used methods for detecting specific nucleic acid sequences generally involve immobilization of the target nucleic acid on a solid support. After the target nucleic acid is fixed on the support, the support is contacted with a suitably labeled nucleotide probe and incubated under hybridizing conditions. After incubation, the solid support is washed to remove any unhybridized probes. The presence of hybridized material on the support is then detected by autoradiography or by spectrometric methods.

The nucleotide probe is typically formed by incorporating a modified nucleotide into an oligonucleotide which facilitates separation or detection of the target sequence. -Several factors go into evaluating the suitability of the modified nucleotide as a separation or detection means. The modified nucleotide must contain a unique substituent that is not normally found on nucleotides. The substituent must react specifically with reagents to provide adequate separation or sensitive detection, whether the modified nucleotide is part of a single-stranded or double-stranded polynucleotide. The substituent can not interfere with normal nucleotide interactions so that the modified nucleotide is still able to bind to other bases, i.e., the substituent, of which there may be several on a single modified nucleotide, must not interfere with hybridization. Lastly, the substituent must be bound to the modified nucleotide in such a manner that it will withstand the experimental conditions of hybridization and the subsequent separation and detection.

2. Description of the Related Art

An excellent overview of chemically modified nucleotides is presented in Englisch, et al., *Angewandte Chemie* (Int. Ed. Engl.) 30(6):613–629 (1991). Chemically labeled nucleotides are also generally disclosed in Stavrianopoulos, et al., U.S. Pat. No. 4,994,373, which discloses labels bound, directly or indirectly by a bridging entity, to a nucleotide probe. Johnston, European Patent Application No. 0,123,300 A2 discloses avidin-biotin-enzyme conjugates used to detect biotinylated nucleotides.

Nucleotide probes can be labeled at the 5' or 3' end such as is disclosed in Brakel, et al. U.S. Pat. No. 5,082,830.

Some methods involve labeling a modified base on one or more nucleotides. Ruth, U.S. Pat. No. 4,948,882 discusses the incorporation of altered purine or pyrimidine bases into chemically synthesized oligonucleotides, where the base has a covalently attached linker arm containing a reporter group.

Ward, et al., U.S. Pat. No. 4,711,955 discloses a nucleotide having a detectable moiety chemically bound to a purine, pyrimidine or 7-deazapurine bonded to the 1-position of the sugar moiety. Stavrianopoulos, U.S. Pat. No. 4,707,440 discusses binding biotin or metal chelating compounds to the base of a nucleotide. Heller, et al., U.S. Pat. No. 4,996,143 pertains to the attachment of donor and acceptor fluorophores to a base via linker arms.

Nucleotides can be modified on the sugar moiety, such as is disclosed in Engelhardt, et al., European Patent Application No. 0,302,175 A2, where a substituent is placed on the C2' or the C3' position of the sugar moiety. Various positions on the base and phosphate are also disclosed.

Nucleotides modified at the 1' position are disclosed in Azhayev, et al., *Tetrahedron Letters* 34(40):6435–6438 (1993) and in Dan, et al., *Bioorganic & Medicinal Chemistry Letters* 3(4):615–618 (1993).

Altered nucleotides have found utility outside the diagnostics field. For example, nucleosides substituted at the 4' position have been shown to have antiviral activity in Maag, et al., European Patent Application No. 0,457,326 A1, and HIV-inhibitor activity in O-Yang, et al., *Tetrahedron Letters* 33(1):37–40 (1992) and Maag, et al., *Journal Of Medicinal Chemistry* 35:1440–1451 (1992). Halazy, et al., European Patent Application No. 0,479,640 A2 discusses nucleosides modified at the phosphate that have antiviral activity. Nucleotides modified at the C5 position of uracil have also shown antiviral and antineoplastic activity in Bergstrom, et al., U.S. Pat. No. 4,247,544.

As described above, most of the modifications fall into one of several categories: modification at the 5' or 3' end; modification of a base; modification of the sugar; and modification at the phosphate. In spite of the advancements in the art, there remains a continuing need to develop improved methods of modifying nucleotides. The end-modification has somewhat limited utility and the base and phosphate modification affect hybridization. Accordingly, there is a continuing need to discover versatile ways to modify nucleotides so that minimal interference with hybridization occurs.

SUMMARY OF THE INVENTION

The present invention pertains to oligonucleotides containing one or more nucleotides that have a substituent other than hydrogen at the 4' position of the sugar moiety. The 4'-substituents facilitate the modification, separation or detection of the oligonucleotide when it is hybridized to a target nucleic acid. These 4'-substituted nucleotides have the structure:

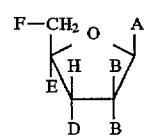

where:

A is a purine or a pyrimidine;

B and B' are selected from the group consisting of H, OH, F, OCH$_3$ and SCH$_3$, provided that at least one is H;

D' is selected from the group consisting of OH, O-P (O) (OH)-OX, O-P(S) (OH)-OX, O-P(S) (SH)-OX and O-P(O) (CH$_3$)-OX, where X is selected from the group consisting of H, a nucleotide, and a protecting group;

E' (the 4' position) is RY, where Y is selected from the group consisting of H and a substituent that renders said nucleotide modifiable, separable or detectable and R is a linking group; and F is selected from the group consisting of OH and O-P(O)(OH)-OX, where X is selected from the group consisting of H, a nucleotide and a protecting group.

One embodiment of the invention relates to the use of these oligonucleotides as nucleotide probes in an improved method of detecting the presence or amount of a target nucleic acid in a sample suspected of containing the target nucleic acid, comprising the steps of: (a) providing in combination a medium suspected of containing the target and at least one nucleotide probe capable of binding to a region of the target; and (b) determining whether the probe has become bound to the target nucleic acid, where the improvement is that the probe has at least one nucleotide that has a substituent other than hydrogen at the 4' position of the sugar moiety.

Another embodiment of the invention pertains to the use of these oligonucleotides as nucleotide probes in a method for detecting the presence of a polynucleotide analyte in a sample suspected of containing the polynucleotide analyte, comprising the steps of: (a) providing in combination a medium suspected of containing the analyte and at least one nucleotide probe capable of binding to a region of the analyte, where the probe has at least one nucleotide that has a substituent other than hydrogen at the 4' position of the sugar moiety which is capable of facilitating the detection of the probe; and (b) determining whether the probe has become bound to the analyte thereby indicating the presence of the analyte.

These oligonucleotides containing one or more 4'-substituted nucleotides can also be packaged in diagnostic assay kits.

Another embodiment of the invention concerns use of oligonucleotides containing one or more 4'-substituted nucleotides as therapeutic agents.

Still another embodiment of the invention is an improved method of producing an oligonucleotide using standard techniques such as a DNA synthesizer, where the improvement is the step of incorporating into the oligonucleotide at least one nucleotide having a substituent other than hydrogen at the 4' position of the sugar moiety which produces, or is capable of producing, the alteration of the oligonucleotide.

DESCRIPTION OF THE SPECIFIC EMBODIMENTS

This invention relates to oligonucleotides, which contain at least one nucleotide that is substituted at the 4' position of the sugar moiety with a substituent other than hydrogen. Substitution at the 4' position in the present invention has been found to only minimally affect the formation of duplex DNA. The 4'-substituent extends unhindered into the minor groove of duplex DNA (Saenger, W. "Principles of Nucleic Acid Structure", Springer Verlag, N.Y. 1984) and the attachment of 4'-substituents at more than one nucleotide unit within a single oligonucleotide has also been shown to only minimally affect duplex DNA in the present invention. This allows for not only the attachment of multiple labels to an oligonucleotide, but also modification of the oligonucleotide concurrently with different labels. Multiple modifications can not be achieved with substituents that are conventionally attached to either the 3' or 5' end. In addition, attachments within an oligonucleotide such as at abasic linkers are typically only possible once within an oligonucleotide because of their severe impact on hybridization properties. Recently described work with modifications at the 1' position (Dan, et al., supra) suffers from the fact that the group points to the interior of the duplex DNA. This is supported by the severe change in melting temperature (−4° C.) shown for a single modification in the middle of the oligonucleotide. More than two modifications at the 4' position in the present invention are tolerated before the effect on duplex DNA is noticeable to the level of a single modification at the 1' position. Therefore, modifications at the 4' position are unique in that they are possible at multiple positions within an oligonucleotide and in that they only minimally affect duplex DNA formation with the target sequence. In addition, modification at the 4' position has been shown in the present invention to lower the $T_m$ of the modified oligonucleotide to its complement by only a small amount, as described in the examples herein. These small changes are significantly less than is found with other labeling techniques. This indicates that the complex formed between the 4'-modified oligonucleotide and the target DNA is quite stable compared to oligonucleotides labeled in other positions. Stable complexes are an advantage when, for instance, washing procedures are utilized in diagnostics to remove background signal, i.e, when the complex that is being detected is stable, a more rigorous washing step can be used.

These oligonucleotides containing 4'-substituted nucleotides find particular utility as nucleotide probes in hybridization assays. One or more of the 4'-substituted nucleotides is incorporated synthetically into an oligonucleotide and used to modify, separate, or detect target nucleic acids that bind to the oligonucleotide.

The term "4'-substituted sugar moiety" is used herein to mean a nucleotide in which the hydrogen at the 4' position of the sugar moiety has been replaced by a linking group bound to hydrogen or to a substituent that renders the nucleotide modifiable, separable or detectable, as defined in the present specification. The sugar moiety is attached to the natural position of a purine (the 9-position) or pyrimidine (the 1-position) or to the equivalent position in an analog. Further, the nucleotide can have one, two or three phosphoryl groups.

This invention also encompasses nucleosides that have been substituted at the 4' position as described above.

In particular this invention pertains to oligonucleotides containing one or more 4'-substituted nucleotides having the structure:

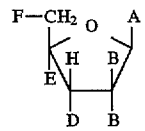

where:

A is a purine or a pyrimidine;

B and B' are selected from the group consisting of H, OH, F, OCH$_3$ and SCH$_3$, provided that at least one is H;

D' is selected from the group consisting of OH, O-P(O)(OH)-OX, O-P(S)(OH)-OX, O-P(S)(SH)-OX and O-P(O)(CH$_3$)-OX, where X is selected from the group consisting of H, a nucleotide, and a protecting group;

E' (the 4' position) is RY, where Y is selected from the group consisting of H and a substituent that renders said nucleotide modifiable, separable or detectable and R is a linking group; and F is selected from the group consisting of OH and O-P(O)(OH)-OX, where X is selected from the group consisting of H, a nucleotide and a protecting group.

When the oligonucleotides are to be used as nucleotide probes in a diagnostic assay, then preferably: B and B' are selected from the group consisting of H, OH and F, provided that at least one is H; and D' is selected from the group consisting of OH and O-P(O)(OH)-OX, where X is selected from the group consisting of H, a nucleotide, and a protecting group.

When the oligonucleotides are to be used as therapeutic agents or in a therapeutic formulation, then preferably: B and B' are selected from the group consisting of H, OCH$_3$ and SCH$_3$, provided that at least one is H; and D' is selected from the group consisting of O-P(S)(OH)-OX, O-P(S)(SH)-OX and O-P(O)(CH$_3$)-OX, where X is selected from the group consisting of H, a nucleotide, and a protecting group; or the corresponding pharmaceutically acceptable ester or salt thereof.

As mentioned above, the oligonucleotides of this invention contain at least one of the 4'-substituted nucleotides described above. The oligonucleotides can contain as many 4'-substituted nucleotides as is chemically feasible. Typically, however, there will be from 1 to 10 4'-substituted nucleotides in an oligonucleotide of this invention. For oligonucleotides useful as nucleotide probes in a hybridization assay, preferably 1 to 4 of the nucleotides will be the 4'-substituted nucleotides described herein. For oligonucleotides useful as therapeutic agents, preferably 1 to 2 of the nucleotides will be 4'-substituted nucleotides.

"Purine" is used herein to mean nitrogenous bicyclic heterocycles, typically including the naturally occurring purines adenine, guanine, xanthine and hypoxanthine. "Pyrimidine" is used herein to mean nitrogenous monocyclic heterocycles, typically including the naturally occurring pyrimidines uracil, thymine and cytosine. These terms, as used herein, also include moieties that have been derivatized or altered by substitution on the parent skeleton, for example, 2-aminopurine; 8-aminopurine; 2,6-diaminopurine; 5-alkylpyrimidines such as 5-ethyl-2,4,-dioxopyrimidine and 5-propyl-2,4-dioxopyrimidine; 5-halopyrimidines such as 5-fluoromethyl-2,4-dioxopyrimidine, 5-difluoromethyl-2,4-dioxopyrimidine, 5-trifluoromethyl-2,4-dioxopyrimidine, 5-(2-halo-1-ethenyl)-2,4-dioxopyrimidines and 5-halo-2,4-dioxopyrimidines; 5-(1-propynyl)pyrimidine; and the like. These terms, as used herein, also include analogs where the parent skeleton has been altered by substituting a carbon for a nitrogen or substituting a nitrogen for a carbon, such as 9-deazapurine; 7-cyano-7-deazapurine; 8-azapurine; 7-deaza-7-alkylpurines; 4-amino-5-aza-2-oxo-pyrimidine; 6-aza-5-methyl-2,4-dioxopyrimidine; 6-aza-2,4-dioxopyrimidine; 1-deaza-5-methyl-2,4-dioxo-pyrimidine; and the like. All of the aforementioned purine and pyrimidine compounds can be of natural or synthetic origin, isolated or manufactured using exclusively or any combination of chemical, biochemical or enzymological methodology.

Although all nucleotides encompassed within the structure set forth above may be prepared and used in the methods of this invention, certain nucleotides are more readily used and/or synthesized and, therefore, are preferred embodiments of the invention. Thus, although purines and pyrimidines are generally suitable, there are certain preferred ones. These include, by way of illustration and not limitation, adenine, guanine, xanthine, hypoxanthine, uracil, thymine and cytosine.

"Protecting group" is used herein to mean a chemical group that changes a functional group of the nucleotide so as to disguise the chemical reactivity of the functional group and prevent it from undesirably reacting during reactions occurring at other sites on the nucleotide. The protecting group must react selectively in good yield to give a protected site that is stable to the subsequent reactions. The protective group must also be selectively removable in good yield by readily available, preferably nontoxic reagents that do not attack or alter the functional group. See for example, T. Greene, "The Role of Protective Groups in Organic Synthesis" in *Protective Groups in Organic Synthesis*, Chapter 1 (John Wiley & Sons, 1981). Suitable protecting groups, by way of illustration and not limitation, include phthalyl, carbobenzyloxy, benzyl, benzoyl, trityl, monomethoxytrityl, dimethoxytrityl, acetyl, trifluoroacetyl, trimethylsilyl, t-butyl(dimethyl)silyl, t-butyl(diphenyl)silyl, carbonate, 2-trimethylsilylethyl, methoxymethyl, 2-methoxyethoxymethyl and dihydropyranyl groups.

As indicated above, the 4'-substituted nucleotides in the oligonucleotides of this invention can comprise a substituent "Y" that renders the nucleotide modifiable, separable or detectable. For purposes of discussion, the nucleotide that contains the "Y" substituent shall be described as being modified, separated or detected. However, since the 4'-substituted nucleotide is part of an oligonucleotide, it is to be understood that the "Y" substituent also renders the oligonucleotide modifiable, separable or detectable. Substituent "Y" may be a functional chemical moiety. Alternately, substituent "Y" may be one member of a specific binding pair ("sbp member"), while the other member of the pair aids in the detection or separation of the nucleotide. For example, the other member of the specific binding pair, i.e., the complementary sbp member, may be bound to a detectable label or to a solid support. An sbp member is one of two different molecules, having an area on the surface or in a cavity that specifically binds to and is thereby defined as complementary with the particular spatial and polar organization of the other molecule. Members of the specific binding pair are often referred to as ligand (any compound for which a receptor naturally exists or can be prepared) and receptor (any compound or composition capable of recognizing a particular spatial and polar organization of a molecule, e.g., epitopic or determinant site), for example, an antigen and antibody, respectively. Illustrative sbp members include operator-repressor, nuclease-nucleotide, biotin-avidin, hormones-hormone receptors, nucleic acid duplexes, IgG-protein A, DNA-DNA, DNA-RNA, and the like. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins, and the like.

Substituent "Y" can be incorporated into one or more nucleotides, which are then used in DNA synthesis to form oligonucleotides. Alternatively, the "Y" substituent(s) can be added after DNA synthesis.

It is often desirable to render a nucleotide modifiable at the 4'position. In doing so, the 4'-group subsequently assists in changing the function or activity of the nucleotide. There are several ways that the 4'-group can render the nucleotide modifiable. For example, "modifiable" is used herein to mean that "Y" can be a reactive functional group that facilitates the subsequent modification of the nucleotide. Examples include, by way of illustration and not limitation, NH$_2$, SH, OH, COOH, NHC(O)CF$_3$ and CHO. Various other functional groups and means of incorporating them into nucleotides are disclosed in MacMillan, et al., *Tetrahedron* 47(14/15):2603–2616 (1991). The nucleotide containing the functional group can be modified before oligonucleotide synthesis. However, it is often desirable to alter a nucleotide after it has been incorporated into a nucleotide sequence.

Therefore, prior to oligonucleotide synthesis, a "Y" functional group can be positioned at the 4' position. In that way, the nucleotide can be incorporated into an oligonucleotide as an intermediate and "Y" can attach to or be replaced by the desired substituent after DNA synthesis. Therefore, when "Y" is a functional group, such substituted nucleotides find particular utility as intermediates in the synthesis of a different nucleotide where the functional group is subsequently linked to or replaced with, for example, an sbp member or label that renders the nucleotide separable or detectable.

"Modifiable" is also used herein to mean that "Y" can be a group that facilitates the subsequent modification of the target or of the duplex formed by the hybridization of an oligonucleotide containing one or more of the altered nucleotides and its complementary sequence, i.e., the target. It may be desirable to have a reactive functionality at the 4' position that can intercalate or catalyze a reaction that will modify the target nucleic acid to which the oligonucleotide is bound. Intercalating groups are also useful in strengthening the binding of the oligonucleotide and thus reducing its tendency to dissociate during washing in an assay, for example. Cleaving of a nucleic acid target, such as an amplicon, can be useful, for example, to prove the presence of a particular sequence recognized by the probe. Examples of such "Y" groups include nucleic acid modifying catalysts; groups that strengthen the duplex such as DNA intercalators and minor groove binders; and groups that allow for cleavage of the hybridized region such as cleavage agents.

Suitable nucleic acid modifying catalysts include, by way of illustration and not limitation, nucleases, methylases and metal chelates.

Suitable DNA intercalators include, by way of illustration and not limitation, ethidium and ethidium bromide; acridines such as acridine orange, proflavine and quinacrine; phenazine and phenazinium salts; pyrenes and diazapyrenes; psoralen and psoralen analogs; and anthraquinones. Oligonucleotides modified with these groups can be used as therapeutic agents to modulate or inhibit the biological processes that involve such nucleic acids. For example, psoralen and acridine moieties are able to intercalate between two base pairs of DNA to inhibit DNA transcription and replication, and phenazinium moieties improve binding after hybridization. Other examples of suitable groups are disclosed in Englisch, et al., *Angewandte Chemie* (Int. Ed. Engl.) 30(6):613–629 (1991), which is incorporated herein by reference.

Minor groove binders are compounds that strengthen the helix, in particular a triple helix, by binding to the minor groove of the helix and include, by way of illustration and not limitation, distamycin, netropsin and bis-benzimidazoles such as commercially available Hoechst 33258, and their analogs.

Cleavage agents are particularly useful for identifying DNA sequence elements when the oligonucleotide is used as a nucleotide probe. Cleavage agents directed by a nucleotide probe to a particular nucleic acid sequence are known to be useful for mapping of high molecular weight DNA (Derva, *Nature* 359:87–88 (1992)). An extension of this finding could include the detection of sequence elements in a sample DNA or an amplified DNA by specific cleavage of the DNA in a predictable fashion. The probe-cleavage agent reagent could allow specific detection of nucleotide sequences that are diagnostic, i.e., indicative of a disease state or infectious agent. Cleavage agents are also useful when the oligonucleotide is to be used as a therapeutic agent. The oligonucleotide, having at least one nucleotide having a cleavage agent at the 4'-position, binds to the target DNA or RNA and cuts the target at the desired region, thus preventing transcription or translation.

Suitable cleavage agents include metal complexes such as, by way of illustration and not limitation, platinum, iron porphyrin complexes, iron ethylenediaminetetraacetic acid complexes, copper phenanthroline and copper bispyridinyl. These compounds work without the addition of light. Other examples are disclosed in Englisch, et al., supra. Photocleavage agents are also suited for use in this invention and include DNA intercalators that can be photo-chemically activated to induce strand cleavage and include, by way of illustration and not limitation, ethidium bromide; acridines such as proflavine and quinacrine; phenazinium salts; pyrenes; psoralen and psoralen analogs; and anthraquinones.

"Separable" is used herein to mean that "Y" is a group that facilitates separation of the nucleotide. For example, "Y" can be a specific binding pair member such as biotin; it renders the nucleotide "separable" because the nucleotide can then be separated from other components by the addition of the complementary specific binding pair member such as avidin or streptavidin, bound to or coated onto a solid phase.

The solid phase is typically a support or surface, which is a porous or non-porous water insoluble material that can have any one of a number of shapes, such as strip, rod, particle, including beads and the like. Suitable materials are well known in the art. See, for example, Ullman, et al. U.S. Pat. No. 5,185,243, columns 10–11, which is incorporated herein by reference. Binding of sbp members to the supports or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970).

"Detectable" is used herein to mean that "Y" is a group that facilitates detection of the nucleotide. "Y" can be a directly detectable group when it is a detectable label that gives off a signal by itself, such as an isotopic label. "Y" can also be a directly detectable group when it is a detectable label that requires other members of a signal producing system in order to be detected, such as when the detectable label is an enzyme and substrate is required to produce a signal. "Y" can be an indirectly detectable group when it is an sbp member used in conjunction with a detectable label that is bound to the complementary sbp member. In this manner, "Y" is indirectly detected by being bound through a specific binding reaction, to a detectable substance. For example, "Y" can be biotin, which is detected by avidin bound to a detectable label such as an isotope or an enzyme. "Y" substituents that are able to be detected indirectly include polynucleotides such as a polynucleotide primer or a specific polynucleotide sequence that can act as a ligand for a complementary polynucleotide or provide a template for amplification or ligation or act as a ligand such as for a repressor protein; haptens; antigens such as digoxin; antibodies; receptors such as avidin; ligands such as biotin and the like.

Suitable labels include, by way of illustration and not limitation, enzymes such as alkaline phosphatase and horseradish peroxidase, ribozyme, a substrate for a replicase such as QB replicase, promoter, dye, fluorescers such as fluorescein, fluorescein isothiocyanate and rhodamine compounds, chemiluminescers such as isoluminol, sensitizers, coenzyme, enzyme substrate, radioactive group, a particle such as latex or carbon particle, metal sol, crystallite, liposome, cell, etc., which may or may not be further labeled with a dye, catalyst or other detectable group and the like. Suitable enzymes and coenzymes are disclosed in Litman, et al., U.S. Pat. No. 4,275,149, columns 19 to 28, and Boguslaski, et al., U.S. Pat. No. 4,318,980, columns 10 to 14; suitable fluorescers and chemiluminescers are disclosed in Litman, et al., supra, at columns 30 and 31; which disclosures are all incorporated herein by reference. Alternatively, as indicated above, "Y" can be an sbp member and the label can become bound thereto by being bound to an sbp member complementary to "Y".

Along with the detectable label, the signal producing system includes any other reagents that may be required to produce a measurable signal, which can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like. A detailed discussion of suitable signal producing systems can be found in Ullman, et al. U.S. Pat. No. 5,185,243, columns 11–13, which is incorporated herein by reference.

As indicated above, substituent "Y" is bound to the compound by a linking group. "Linking group" is used herein to mean any of the well known bonds including carbon-carbon single bonds, carbon-carbon double bonds, carbon-nitrogen single bonds and carbon-oxygen single bonds, and typically contains from 1–20 atoms, not including hydrogen atoms. The linking group serves to position substituent "Y" so that it is able to interact with reagents that facilitate the modification, separation or detection of the nucleotide. Suitable linking groups, by way of illustration and not limitation, include alkylene, alkyl, alkenyl, alkadienyl, aralkyls such as (4-ethyl)phenethyl and (4-propyl) phenpropyl, aminoalkyls such as N-(N-(2-aminoethyl)-2-aminoethyl) aminomethyl and N-(N-(3-aminopropyl)-3-aminopropyl) aminomethyl, alkylethers such as (2-hydroxyethoxy) ethoxymethyl and (3-hydroxypropoxy) propoxymethyl and combinations such as N-(2-aminoethyl)-2-aminoethoxymethyl.

The general synthetic approach for introducing the substituents of A, B, B', D' and F are well known in the art. Many of the starting materials and other compounds used in the synthesis are commercially available from sources such as Aldrich Chemical Company or Sigma Chemical Company; and where not, they can easily be prepared according to procedures that are well known in the art. See for example, Zorbach and Tipson, eds., *Synthetic Procedures in Nucleic Acid Chemistry*, Vol. 1, Wiley Interscience (1988) and Townsend and Tipson, eds. *Nucleic Acid Chemistry*, Parts 1–3, Wiley Interscience (1978, 1978, 1986).

Placing the non-hydrogen substituent, E', at the 4' position of the sugar moiety of a nucleotide and incorporating one or more of these 4'-substituted nucleotides into oligonucleotides is novel and oligonucleotides of this invention may be prepared by a process that involves the steps described below.

It is preferred that each of the compounds and intermediates described in each reaction of the synthesis be isolated and/or purified prior to its use as a starting material in the subsequent reaction. Such isolation and purification can be accomplished by numerous techniques that are well known in the art. These include, for example, evaporation, filtration, extraction, crystallization, column chromatography, thin-layer chromatography, thick-layer chromatography, or a combination of these procedures. Specific illustrations of suitable isolation and purification procedures can be had by reference to the examples set forth below. However, other isolation and purification techniques can also be used.

In general, the starting material for the compounds of this invention are typically thymidines that undergo a five step sequence similar to that disclosed in O-Yang, et al., *Tetrahedron Letters* 33(1):37–40 (1992) to protect the 3' position and to place a reactive functional group at the 4' position.

The 4'-group is then oxidized, for example by a Swern oxidation, followed by protection of the 5' position. Protecting the 5' position can be accomplished by reacting the compound with a slight excess of a suitable acid-labile protecting reagent. These include, for example, tritylchlorides such as monomethoxytrityl chloride, dimethoxytrityl chloride (DMTrCl), trimethoxytrityl chloride and the like. Dimethoxytrityl chloride is a particularly suitable reagent as it is compatible with DNA synthesis procedures. The protecting reaction is carried out in a suitable solvent such as, for example pyridine, lutidines, trialkylamines and the like. The reaction takes from 1 to 48 hours and is done at temperatures in the range of –20° C. to 120° C., preferably 20° C. to 100° C., more preferably about room (or ambient) temperature, e.g., about 20° C.

A reactive functional group can then be placed at the 4' position of the 4'-oxidized/5'-protected compound by a Wittig reaction with a compound such as 5-hexenyltriphenylphosphonium bromide, which is formed by reacting a halogenated alkene with a compound such as triphenylphosphine. The 4'-oxidized/5'-protected compound can also be reacted with an amine in a reductive amination reaction. Thus, the 4'-oxidized/5'-protected compound is converted to a 4'-functional group/5'-protected compound.

This 4'-functional group/5'-protected compound is then subjected to hydroboration to yield a 4'-hydroxylated compound. The 4'-hydroxyl group is then converted to an azide, by a two step reaction: 1) reaction with a compound such as methanesulfonyl chloride to replace the 4'-hydroxy group with a methanesulfonyloxy group, and then 2) reaction with an alkaline metal azide, such as sodium or lithium azide, preferably sodium azide, to replace the 4'-methansulfonyloxy group with an azido group. Alternatively, the alcohol can be converted to the azide in one step by reaction with a reagent such as diphenylphosphoryl azide.

The next step involves protecting the functional or chemically reactive sites on the compound during the synthesis of the nucleotide probe using standard reagents that will permit deprotection in the final step of the synthesis. For example, the 4'-reactive azide group can first be reduced to an amine using standard reducing agents such as 1,3-propanedithiol, then the amine protected by reaction with trifluoroacetate or trifluoroacetyl anhydride. Protection can be easily accomplished using any of several suitable protecting groups, as defined above, in numerous suitable solvents such as alcohols, pyridines, lutidines, chloroform, and the like, by reaction of the nucleosides with an appropriate reducing agent for one or more days, followed by reaction with an excess of appropriate acid anhydride for about 1 to 24 hours. Both reactions can be done at temperatures in the range of 0° C. to 110° C., preferably 20° C. to 80° C., more preferably room temperature. Suitable reducing agents include, for example, thiols such as 1,3-propanedithiol and thiophenol, sodium borohydride and sodium cyanoborohydride, triphenylphosphine in the presence of water, zinc, stannous chloride and catalytic hydrogenation catalyzed by a platinum or palladium catalyst. Appropriate acid anhydrides include acetic anhydride, trifluoroacetic anhydride, benzoic anhydride, anisoic anhydride and the like. Preferred acid anhydrides include, acetic, trifluoroacetic, dimethoxyacetic, benzoic and isobutyric anhydride.

The next step involves removal of the 3'-protecting group such as t-butyl dimethylsilyl. Activation to the phosphite analog is typically accomplished by treating the nucleoside with a suitable phosphitylating agent in an appropriate solvent for several hours to one day, at a temperature within the range of −90° C. to 60° C., preferably room temperature. Suitable phosphitylating agents include, for example, methylphosphodichloridite, o- and p-chlorophenylphosphodichloridite, 2-cyanoethyl bis (isopropyl) chlorophosphoramidite, alkylphospho (dialkylamino) monochlorodites such as methylphospho (di-iso-propylamino) monochloridite and the like. Solvents that can be used, include pyridine, lutidines, acetonitrile, tetrahydrofuran, dioxane, dichloromethane, chloroform and the like. Tetrahydrofuran is particularly suitable.

In a preferred embodiment of the invention, the 4'-protected nucleotide is incorporated into a growing nucleotide chain of the oligonucleotide and the desired 4'-substituent added at the completion of the synthesis of the probe. However, this invention also contemplates removal of the 4'-protecting group and positioning of the desired "Y" substituent prior to incorporating one or more of the 4'-modified nucleotides in an oligonucleotide.

The above-procedure is more particularly illustrated as follows for the synthesis of 3'-O-[2-cyanoethyl bis (isopropyl) phosphoramidite ]-5'-O-(4,4'-dimethoxytrityl)-4'-(7-trifluoroacetaido-1-hepten-1-yl)-thymidine (8), which is incorporated into an oligonucleotide that is used as a nucleotide probe, and the desired 4'-substituent (biotin) is added at the completion of the synthesis of the oligonucleotide. The starting material is a thymidine that undergoes a five step sequence similar to that disclosed in O-Yang, supra, to protect the 3' position and to place a reactive functional group at the 4' position to yield 3'-O-[(dimethyl-1,1-dimethylethyl)silyl]-4'-hydroxymethyl-thymidine (1). The 4'-group is then oxidized by a Swern oxidation, followed by protection of the 5' position to yield 5'-O-(4,4'-dimethoxytrityl)-3'-O-[(dimethyl-1,1-dimethylethyl) silyl]-4'-formyl-thymidine (2). Protecting the 5' position can be accomplished by reacting the compound with 4,4'-dimethoxytritylchloride in pyridine. The reaction takes about 20 hours and is done at room temperature. A reactive functional group is then placed at the 4' position of Compound (2) by a Wittig reaction with 5-hexenyltriphenylphosphonium bromide to yield 5'-O-(4, 4'-dimethoxytrityl)-3'-O-[(dimethyl-1,1-dimethylethyl) silyl]-4'-(1,7-heptadien-1-yl)-thymidine (3). Compound (3) is subjected to hydroboration followed by an oxidative workup to yield 5'-O-(4,4'-dimethoxytrityl)-3'-O-[(dimethyl-1,1-dimethylethyl) silyl]-4'-(7-hydroxy-1-hepten-1-yl)-thymidine (4). Compound (4) is then converted to an azide, 5'-O-(4,4'-dimethoxytrityl)-3'-O-[(dimethyl-1,1-dimethylethyl)silyl]-4'-(7-azido-1-hepten-1-yl)-thymidine (5), by a two step reaction: 1) reaction with methanesulfonyl chloride to replace the 4'-hydroxy group with a methanesulfonyloxy group, and then 2) reaction with sodium azide, to replace the 4'-methansulfonyloxy group with an azido group. The 4'-reactive azide group of Compound (5) is then reduced to an amine with 1,3-propanedithiol, then the amine is protected by reaction with ethyl trifluoroacetate for about 24 hours at room temperature to yield 5'-O-(4,4'-dimethoxytrityl)-3'-O-[(dimethyl-1,1-dimethylethyl)silyl]-4'-(7-trifluoroacetamido-1-hepten-1-yl)-thymidine (6). The 3'-protecting group is then removed to yield 5'-O-(4,4'-dimethoxytrityl)-4'-(7-trifluoroacetamido-1-hepten-1-yl)-thymidine (7). Activation to the phosphite analog, 3'-O-[2-cyanoethyl bis(isopropyl) phosphoramiditel]-5'-O-(4,4'-dimethoxytrityl)-4'-(7-trifluoroacetamido-1-hepten-1-yl)-thymidine (8), is accomplished by treating Compound (7) with 2-cyanoethyl bis(isopropyl) chlorophosphoramidite for about 20 hours at room temperature. Then as described above, the desired substituent can be positioned at the 4' position of Compound (8), or the compound can be incorporated into an oligonucleotide and the desired 4'-substituent added after oligonucleotide synthesis.

Various techniques can be employed for preparing the oligonucleotides if the present invention after the nucleotide composition of the desired nucleotide probe or therapeutic oligonucleotide has been determined. As used herein, the term "oligonucleotide" is used to mean a nucleotide sequence at least 4 nucleotides in length. In general, the oligonucleotides of this invention will be about 8 to 300 nucleotides, more frequently 15 to 100 nucleotides in length. The oligonucleotides can be obtained by biological or chemical synthesis. For short sequences (up to 100 nucleotides), chemical synthesis will frequently be more economical as compared to biological synthesis. In addition to economy, chemical synthesis provides a convenient way of incorporating low molecular weight compounds and/or the 4'-substituted nucleotides of this invention during the synthesis step. Furthermore, chemical synthesis is very flexible in the choice of length and region of the target nucleotide sequence. The oligonucleotides can be synthesized by standard methods such as those used in commercial automated nucleic acid synthesizers, which include: the phosphoramidate technique (Caruthers, et al., "Methods in Enzymology," Vol. 154, pp. 287–314 (1988)); the phosphotriester and phosphodiester methods (Narang, et al., *Methods Enzymol* 68:90 (1979)); synthesis on a support (Beaucage, et al., *Tetrahedron Letters* 22:1859–1862 (1981)); and other methods which are disclosed in "Synthesis and Applications of DNA and RNA," Narang, editor, Academic Press, New York, 1987. A particularly preferred method of incorporating the 4'-protected nucleotide into a growing nucleotide chain is by condensation reaction to produce the desired oligonucleotide.

Chemical synthesis of DNA or RNA on a suitably modified glass or resin can result in DNA or RNA covalently attached to the surface. This may offer advantages in washing and sample handling. For longer sequences standard replication methods employed in molecular biology can be used such as those employed in commercial kits for preparation of RNA (e.g. from Promega) and by the use of M13 for single stranded DNA as disclosed in J. Messing, *Methods Enzymol* 101:20–78 (1983).

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

After the oligonucleotide is synthesized, the 4'-protecting group can then be removed and substituted with the desired "Y" substituent that will render the nucleotide modifiable, separable or detectable.

Alternately, as noted above, the 4'-protecting group can be removed and the substituent added prior to DNA synthesis.

Unless specified otherwise, the synthesis reactions take place at atmospheric pressure over a temperature range from about −20° C. to about 100° C., more preferably from about 10° C. to about 50° C. and most preferably at about room temperature. Suitable solvents for the condensation reaction include pyridine, lutidines, acetonitrile, tetrahydrofuran, dioxane, dichloromethane, chloroform and the like.

As mentioned above, one use for oligonucleotides containing one or more 4'-substituted nucleotides is in nucleic acid hybridization techniques for the identification, localization, isolation or quantification of a complementary nucleotide sequence of interest. Such altered oligonucleotides are capable of performing under conditions commonly found in hybridization assays, as are set forth in more detail below.

One embodiment of the invention uses the oligonucleotides as nucleotide probes in a method for detecting the presence of a polynucleotide analyte in a sample suspected of containing the polynucleotide analyte, comprising the steps of: (a) providing in combination a medium suspected of containing the polynucleotide analyte and at least one nucleotide probe capable of binding to a region of the polynucleotide analyte, where the nucleotide probe has at least one nucleotide that has a substituent other than hydrogen at the 4' position of the sugar moiety and where the substituent is capable of facilitating the detection of the nucleotide probe; and (b) determining whether the nucleotide probe has become bound to the polynucleotide analyte thereby indicating the presence of the polynucleotide analyte.

"Polynucleotide analyte" is used herein to mean a compound or composition to be measured that is a polymeric nucleotide or a portion of a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides, since isolation of the analyte from the natural state often results in fragmentation of the polymeric nucleotide. The polynucleotide analytes include nucleic acids from any source in purified or unpurified form including DNA (double and single stranded) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans and fragments thereof and the like. Some examples of biological materials include microorganisms, such as are disclosed in Goodman, et al., U.S. Pat. No. 4,994,368 at columns 5–7, which is incorporated herein by reference. The polynucleotide analyte can be only a minor fraction of a complex mixture such as a biological sample. The analyte can be obtained from various biological materials by procedures well known in the art.

The polynucleotide analyte, where appropriate, may be treated to cleave the analyte to obtain a polynucleotide fragment that contains a target polynucleotide sequence. Such cleaving treatments may be accomplished, for example, by shearing or by treatment with a restriction endonuclease or other site specific chemical cleavage method. Such a cleaved polynucleotide fragment is also referred to herein as a polynucleotide analyte.

For purposes of this invention, the polynucleotide analyte, or a cleaved fragment obtained from the polynucleotide analyte, is usually at least partially denatured or single stranded or treated to render it denatured or single stranded. Such treatments are well-known in the art and include, for instance, heat or alkali treatment.

"Nucleotide probe" is used herein to mean a labeled oligonucleotide sequence that is complementary to a region of the target nucleic acid or polynucleotide analyte. The terms "hybridization" and "binding" are used interchangeably. The ability of two polynucleotide sequences to hybridize with each other is based in a large part on the degree of complementarity of the two nucleotide sequences, which in turn is based on the fraction of matched complementary nucleotide pairs. Because of this complementarity, the probe is capable of binding to the desired region. Binding actually occurs if the target or analyte is present.

Another embodiment of a method in accordance with the present invention uses the oligonucleotides as nucleotide probes in an improved method of detecting the presence or amount of a target nucleic acid in a sample suspected of containing the target nucleic acid, comprising the steps of: providing in combination a medium suspected of containing the target nucleic acid and at least one nucleotide probe capable of binding to a region of the target nucleic acid; and determining whether the nucleotide probe has become bound to the target nucleic acid, where the improvement involves the nucleotide probe having at least one nucleotide that has a substituent other than hydrogen at the 4' position of the sugar moiety.

"Target nucleic acid" is used herein to mean a sequence of nucleotides to be identified, either RNA or DNA, existing within the polynucleotide analyte. The target nucleic acid is at least 100 nucleotides, usually at least 200, frequently 200–4000 nucleotides, in length. Preferably the target nucleic acid is about 200 to 1200 deoxynucleotides. The minimum number of nucleotides is selected to assure that the presence of the target nucleic acid in a medium is a specific indicator of the presence of polynucleotide analyte in a sample, while the maximum number is normally governed by the efficiency of amplification of the sequence but may be also limited by the length of the polynucleotide analyte and its tendency to be broken by shearing, or other processes during isolation and any procedures required to prepare the sample for assay.

As mentioned above, the hybridization methods of this invention combine a medium suspected of containing the analyte and at least one nucleotide probe, i.e., oligonucleotide, of the invention. The medium typically contains a sample suspected of containing the analyte, such as, for example, a serum or urine sample. This sample may be pretreated prior to placement in the medium. The nucleotide probe and medium are then combined under hybridizing conditions such that the probe will hybridize to any polynucleotide analyte or target nucleic acid that is present in the medium.

The determining step may involve a qualitative or quantitative analysis. Any standard method for specifically detecting nucleic acid sequences can be used, facilitated by the nucleotide probe of the invention. Non-hybridized probe is separated from hybridized probe and the presence or amount of analyte can be determined by observing or measuring the amount of hybridized probe. Alternatively, the amount of analyte can be determined by measuring the amount of non-hybridized probe.

The determining step may involve the addition of other reagents to facilitate detection such as members of the signal producing system. For example, if the probe has an enzyme label at the 4' position, the determining step may involve the addition of substrate.

The sample, probe and any other reagents may be combined simultaneously or wholly or partially sequentially. "Wholly or partially sequentially" is used herein to mean when the sample and reagents are combined with one or more of the remaining reagents to form a subcombination. Each subcombination can then be subjected to one or more steps of the present method. Thus, each of the subcombinations can be incubated under conditions to achieve one or more of the desired results.

Appropriate reaction conditions are chosen for carrying out the hybridization assay methods in accordance with the present invention. The following description sets forth suitable conditions, which are subject to modification by those skilled in the art depending on the specific reagents and other molecules chosen for any particular application.

Generally, an aqueous medium is employed. Other polar cosolvents may also be employed in the medium, usually oxygenated organic solvents of from 1–6, more usually from 1–4, carbon atoms, including alcohols, ethers and the like. Usually, these cosolvents are present in less than about 70 weight percent, more usually, in less than about 30 weight percent.

The pH for the medium is usually in the range of about 5.5 to 10, more usually, in the range of about 6.5–9.5 and, preferably, in the range of about 7–9. Various buffers may be used to achieve the desired pH and maintain the pH during the determination, for example, borate, phosphate, carbonate, Tris, barbital and the like. The particular buffer employed is not critical to this invention but in individual methods one buffer may be preferred over another.

Moderate temperatures are normally employed for carrying out the methods of this invention and can range from 20° to 95° C., usually 35° to 90° C., frequently 50° to 80° C. The temperature may vary with the step being undertaken. For example, for hybridization the temperature may be maintained at about 40°–80° C. and increased to 85°–100° C. for amplification.

The assay method is conducted for a time sufficient to achieve the necessary hybridization and amplification. Generally, the time period for conducting the method is from about 5 to 200 minutes, where there are about 20 seconds to 10 minutes per cycle and any number of cycles can be used from 1 to as high as 80 or more, usually 5 to 60, frequently 10–50. As a matter of convenience it is usually desirable to minimize the time period and the number of cycles.

The amount of the target nucleic acid can be as low as one or two molecules in a sample but generally varies from about $10^2$ to $10^{14}$, more usually from about $10^3$ to $10^8$ molecules in sample volumes that may be less than a microliter but will usually be 1–1000 μL, more usually 5–250 μL. The amount of the nucleotide probe should be at least as great as the number of copies desired and is usually present in at least $10^{-9}$ M, preferably $10^{-7}$ M and more preferably at least about $10^{-6}$ M. Preferably, the concentration of the nucleic acid is substantially in excess over, preferably at least 100 times greater than, the concentration of the target nucleic acid. The concentration of the other reagents in an assay generally will be determined by the concentration range of interest of the polynucleotide analyte. A further consideration in determining reagent concentrations is that a sufficient number of copies of extended primer be produced in relation to the polynucleotide analyte so that such copies can be readily detected and provide an accurate determination of the polynucleotide analyte if present.

As a matter of convenience, predetermined amounts of reagents employed in the present invention can be provided in a kit in packaged combination. The kits can be used in accordance with the methods of the present invention in determining a polynucleotide analyte or target nucleic acid. For example, a kit useful in the present invention can comprise in packaged combination with the other reagents, at least one nucleotide probe capable of binding to a region of the analyte or target sequence, where the probe has at least one nucleotide that has a substituent other than hydrogen at the 4' position of the sugar moiety so that the probe can be labeled or bound to a support or can be provided with groups to render the probe labeled or bound to a support. The kit can also contain written instructions on how to use the reagents and/or how to perform a particular assay.

The kit can further include nucleoside triphosphates such as deoxynucleoside triphosphates (dNTPs) such as, e.g., deoxyadenosine triphosphate (dATP), deoxyguanosine triphosphate (dGTP), deoxycytidine triphosphate (dCTP) and deoxythymidine triphosphate (dTTP) or derivatives or analogs of the above, members of a signal producing system and also various buffered media, some of which may contain one or more of the above reagents.

The relative amounts of the various reagents in the kits can be varied widely to provide for concentrations of the reagents that substantially optimize the reactions that need to occur during the present method and to further substantially optimize the sensitivity of any assay performed. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit.

It should be understood that various ancillary materials will frequently be employed in the methods in accordance with the present invention. For example, buffers will normally be present in the medium, as well as stabilizers for the medium and the reaction components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

Another embodiment of the invention is an improved method of producing an oligonucleotide using standard techniques such as a DNA synthesizer, where the improvement involves the step of incorporating into the oligonucleotide at least one nucleotide having a substituent other than hydrogen at the 4' position of the sugar moiety, where the substituent produces, or is capable of producing, the alteration of the oligonucleotide. The 4'-substituted nucleotide is inserted at select positions during standard automated synthesis procedures such as are described above. Such an oligonucleotide can be used in any of the aforementioned hybridization assays or as a therapeutic agent. The incorporating step of this method can involve the step of synthesizing the oligonucleotide using a nucleotide precursor having a substituent other than hydrogen at the 4' position of the sugar moiety. The alteration of the oligonucleotide can further involve the step of hybridizing to the oligonucleotide a polynucleotide that lacks a nucleotide having a 4'-substituent other than hydrogen.

It is also contemplated that the oligonucleotides of this invention, having at least one nucleotide having a substituent other than hydrogen at the 4' position of the sugar moiety, will be useful in antisense type therapy as therapeutic agents having anti-viral or anti-cancer activity.

Depending upon the desired route of administration, the oligonucleotides of this invention, or a pharmaceutically acceptable ester or salt thereof, may be in the form of solid, semi-solid or liquid such as tablets, pills, powders, capsules, liposomes, gels, ointments, liquids, suspensions, or the like. In the preferred embodiment, the oligonucleotides are administered in unit dosage forms suitable for single administration of precise dosage amounts, i.e., a pharmaceutically effective amount. The composition may also include pharmaceutically acceptable vehicles or carriers, diluents, and other pharmaceutical agents, adjuvants and stabilizers, such as are commonly utilized in pharmaceutical formulations for treatment of animals and humans. Effective amounts of these additional components will be amounts which are sufficient to obtain pharmaceutically acceptable formulations in terms of solubility of components and biological activity, to name a few considerations.

The invention is demonstrated further by the following illustrative examples.

EXAMPLE 1

Synthesis of 4'-Biotinylated Nucleotide

A). Synthesis of 3'-O-[(dimethyl-1,1-dimethylethyl)silyl]-4'-hydroxymethyl-thymidine (1).

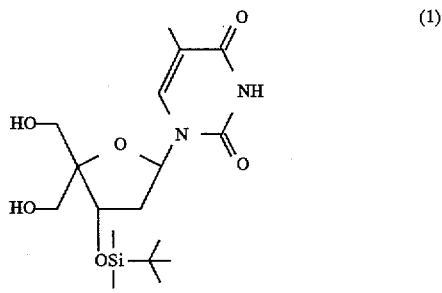

Thymidine was converted to 3'-O-[(dimethyl-1,1-dimethylethyl)silyl]-4'-hydroxymethyl-thymidine (1) by the five step sequence disclosed in the literature (O-Yang, et al., supra).

B). Synthesis of 5'-O-(4,4'-dimethoxytrityl)-3'-O-[(dimethyl-1,1-dimethylethyl)silyl]-1,4'-formyl-thymidine (2).

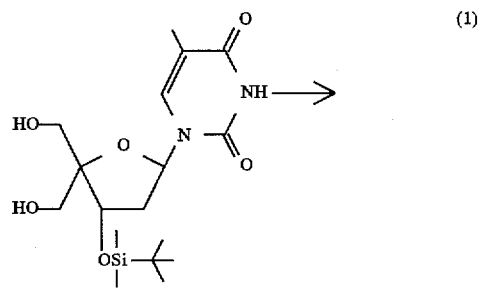

To a solution of oxalylchloride (0.575 mL, 6.5 mmole) in dichloromethane (10 mL) at −70° C., was added dimethylsulfoxide (0.47 mL, 6.5 mmole). The mixture was stirred at −70° C. for 30 minutes before a solution of Compound (1) (2.4 g, 6.2 mmole) in dichloromethane (18 mL) was added. Stirring at −70° C. was continued for 150 minutes. Triethylamine (4.3 mL, 31 mmole) was added dropwise and the reaction mixture was allowed to warm to room temperature over a 20 hour period. The reaction was quenched by the addition of methanol (2 mL), followed 10 minutes later by 60 mL of water. The phases were separated. The aqueous phase was extracted three times with dichloromethane (60 mL each). The combined organic extracts were washed with solutions of dilute hydrochloric acid followed by saturated sodium bicarbonate and brine. After drying the organic extracts over magnesium sulfate, the solvent was removed under reduced pressure to provide 3'-O-[(dimethyl-1,1-dimethylethyl) silyl]-4'-formyl-thymidine (1.88 g) in crude form as a white solid.

To the crude 3'-O-[(dimethyl-1,1-dimethylethyl)silyl ]-4'-formyl-thymidine (1.88 g) was added pyridine (12 mL) followed by 4,4'-dimethoxytritylchloride ("DMTrCl") (2.48 g, 7.4 mmole) and 4-dimethylaminopyridine (0.12 g, 0.1 mmole). The mixture was stirred at room temperature for 20 hours and the reaction was quenched by the addition of methanol (1.0 mL). The reaction mixture was poured into water (60 mL) and was extracted three times with dichloromethane (70 mL each). The combined organic extracts were washed with half saturated brine and dried over magnesium sulfate. Evaporation under reduced pressure gave 6.62 g of a yellow oil which was chromatographed on a silica gel column using hexane/ethyl acetate mixtures for elution. The product fractions were combined to provide 1.38 g (32.4%) of 5'-O-(4,4'-dimethoxytrityl)-3'-O-[(dimethyl-1,1-dimethylethyl) silyl]-4'-formyl-thymidine (2) as a foam. NMR analysis indicated that the material was approximately 80% pure.

C). Synthesis of 5-hexenyltriphenylphosphonium bromide.

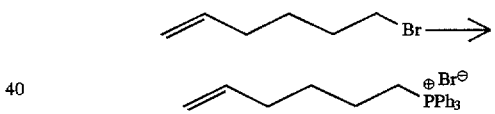

To a solution of triphenylphosphine ("PPh₃") (9.65 g, 36.8 mmole) in benzene (12 mL) was added 6-bromo-1-hexene (5 g, 30.7 mmole) and the resulting mixture was heated under reflux for 18 hours. Upon cooling, a white precipitate formed, which was filtered off and washed twice with benzene before drying under high vacuum. 9.08 g (70%) of 5-hexenyltriphenylphosphonium bromide was obtained.

D). Synthesis of 5'-O-(4,4'-dimethoxytrityl)-3'-O-[(dimethyl-1,1-dimethylethyl)silyl]-4'-(1,7-heptadien-1-yl)-thymidie (3).

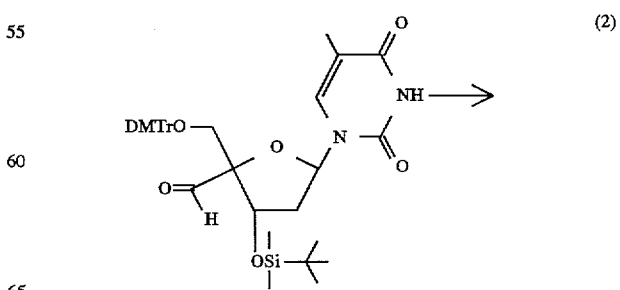

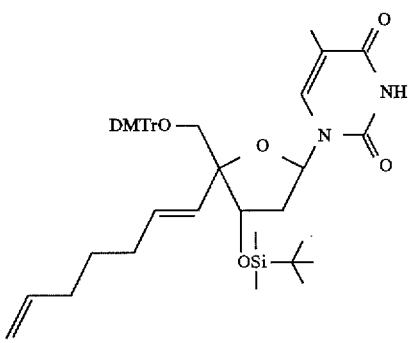

To dry dimethylsulfoxide ("DMSO") (6 mL) was added sodium hydride (97%, 148 mg, 6.4 mmole) under nitrogen and the resulting mixture was heated to 60°–65° C. for 2 hours. The mixture was cooled to room temperature and 5-hexenyl-triphenylphosphonium bromide (2.94 g, 6.9 mmole) was added under stirring. The mixture was again heated to 60°–65° C. for 40 minutes and cooled to 5° C. with a ice/water bath. To this red solution was added dropwise a solution of Compound (2) (1.38 g, 80% pure, ca. 1.6 mmole) in DMSO (6 mL). Stirring was continued at the end of the addition for 10 minutes at 5° C. and the reaction mixture was diluted with dichloromethane (10 mL) and poured into ice cold water (50 mL). The organic phase was separated and the aqueous phase was re-extracted twice with dichloromethane (50 mL each). The combined organic extracts were dried over magnesium sulfate and concentrated to a red oil under reduced pressure. This oil was chromatographed on silica gel using ethyl acetate/hexane solvent mixtures to provide 5'-O-(4,4'-dimethoxytrityl)-3'-O-[(dimethyl-1,1-dimethylethyl)silyl]-4'-(1,7-heptadien-1-yl)-thymidine (3) (0.79 g, 65%) as an off-white solid. Recrystallizations from hot hexane provided a sample with m.p. 83° C.

E). Synthesis of 5'-O-(4,4'-dimethoxytrityl)-3'-O-[(dimethyl-1,1-dimethylethyl)silyl]-4'-(7-hydroxy-1-hepten-1-yl)-thymidine (4).

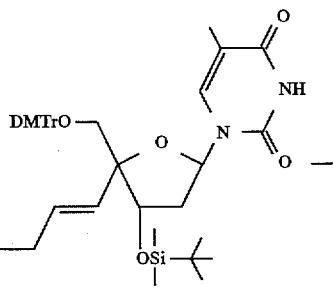

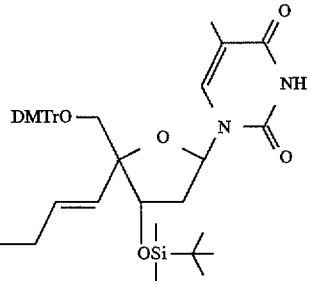

A borane-methyl sulfide complex (60 μL, 10M in THF, 1.78 mmole) was added dropwise to a solution of Compound (3) (447 mg, 0.59 mmole) in tetrahydrofuran (2.5 mL) at 0° C. under nitrogen. The reaction mixture was stirred at 0° C. for 2 hours before a solution of sodium perborate (274 mg, 1.78 mmole) in water (5 mL) was added. Stirring was continued at room temperature for 2 hours and the reaction mixture was diluted with ether (20 mL) and the phases separated. The aqueous phase was re-extracted twice with ether (30 mL each) and the combined organic extracts were washed with brine (10 mL) and dried over magnesium sulfate. Removal of the solvent under reduced pressure gave a colorless oil (0.74 g). Purification was achieved through chromatography on silica gel using ethyl acetate/hexane solvent mixtures to provide 540 -O-(4,4'-dimethoxytrityl)-3'-O-[(dimethyl-1,1-dimethylethyl) silyl]-4'-(7-hydroxy-1-hepten-1-yl)-thymidine (4) (0.289 g, 64%) as a white foam.

F). Synthesis of 5'-O-(4,4'-dimethoxytrityl)-3'-O-[(dimethyl-1,1-dimethylethyl)silyl]-4'-(7-azido-1-hepten-1-yl)-thymidine (5).

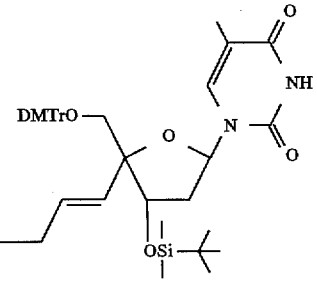

Synthesis of 5'-O-(4,4'-dimethoxytrityl)-3'-O-[(dimethyl-1,1-dimethylethyl)silyl)]-4'-(7-azido-1-hepten-1-yl)-thymidie (5) involved a two-step process, where Compound (4) was converted to 5'-O-(4,4'-dimethoxytrityl)-3'-O-[(dimethyl-1,1-dimethylethyl) silyl]-4'-(7-methanesulfonyloxy-1-hepten-1-yl)-thymidine, which then was converted to the desired product (5), as described below:

1. Synthesis of 5'-O-(4,4'-dimethoxytrityl)-3'-O-[(dimethyl-1,1-dimethylethyl)silyl]-4'-(7-methanesulfonyloxy-1-hepten-1-yl)-thymidine.

Methanesulfonyl chloride (96 µL, 1.22 mmole) was added dropwise to Compound (4) (250 mg, 0.32 mmole) in dry pyridine (3 mL) at 0° C. under nitrogen. The mixture was stirred at 0° C. for 2 hours and the reaction was quenched by the dropwise addition of methanol (1.5 mL). The yellow solution was poured into water (20 mL) and the layers were separated. The organic phase was washed with brine (20 mL), dried over magnesium sulfate and concentrated to a white solid (0.41 g) under reduced pressure. (Routinely, this crude material was used directly in the next step). The crude product (0.41 g) was purified by column chromatography on silica gel using ethyl acetate/hexane mixtures for elution. 5'-O-(4,4'-dimethoxytrityl)-3'-O-[(dimethyl-1,1-dimethylethyl) silyl]-4'-(7-methanesulfonyloxy-1-hepten-1-yl)-thymidine (241 mg, 87.5%) was obtained as a white solid. Recrystallization from hexane/dichloromethane gave a sample with m.p. 72°–75° C.

2. Synthesis of 5'-O-(4,4'-dimethoxytrityl)-3'-O-[(dimethyl-1,1-dimethylethyl)silyl]- 4'-(7-azido-1-hepten-1-yl)-thymidine (5).

5'-O-(4,4'-dimethoxytrityl)-3'-O-[(dimethyl-1,1-dimethylethyl) silyl]-4'-(7-methanesulfonyloxy-1-hepten-1-yl)-thymidine (219 mg, 0.25 mmole), sodium azide (100 mg, 1.5 mmole) and tetrabutyl ammonium iodide (10 mg, 0.025 mmole) were placed in a dry flask under nitrogen and benzene (5 mL) was added. The mixture was heated under reflux for 14 hours, poured onto ice (15 mL) and extracted four times with dichloromethane (30 mL each). The combined organic extracts were washed with brine (20 mL), dried over magnesium sulfate and the solvent was removed under reduced pressure to provide a white solid. Chromatography on a silica gel column with ethyl acetate/hexane mixtures gave 5'-O-(4,4'-dimethoxytrityl)-3'-O-[(dimethyl-1,1-dimethylethyl)silyl]-4'-(7-trifluoroacetamido-1-hepten-1-yl)-thymidine (5) (192 mg, 94%), m.p. 72°–74° C.

G). Synthesis of 5'-O-(4,4'-dimethoxytrityl)-3'-O-[(dimethyl-1,1-dimethylethyl)silyl]-4-(7-trifluoroacetamido-1-hepten-1-yl)-thymidine (6).

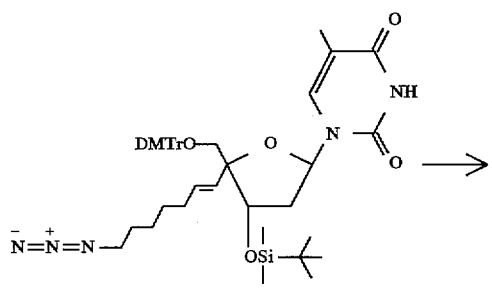

(5)

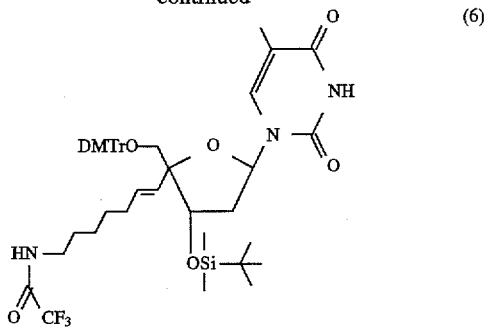

(6)

To Compound (5) (450 mg, 0.56 mmole) in dry methanol (7.5 mL) was added under stirring 1,3-propanedithiol (0.284 mL, 2.82 mmole) followed by triethylamine (0.394 mL, 2.82 mmole). The mixture was stirred at room temperature for 5 days. The mixture was diluted with methanol (7 mL) and ethyl trifluoroacetate (0.675 mL, 5.6 mmole) and triethylamine (0.237 mL, 1.7 mmole) was added. Stirring at room temperature was continued for 24 hours. The resulting suspension was diluted with dichloromethane (5 mL) and the solvent was removed under reduced pressure. Column chromatography on silica gel with ethyl acetate/hexane mixtures gave 5'-O-(4,4'-dimethoxytrityl)-3'-O-[(dimethyl-1,1-dimethylethyl) silyl]-4'-(7-trifluoroacetamido-1-hepten-1-yl)-thymidine (6) (371 mg, 76%), m.p. 75°–76° C.

H). Synthesis of 5'-O-(4,4'-dimethoxytrityl)-4'-(7-trifluroacetamido-1-hepten-1-yl)-thymidine (7).

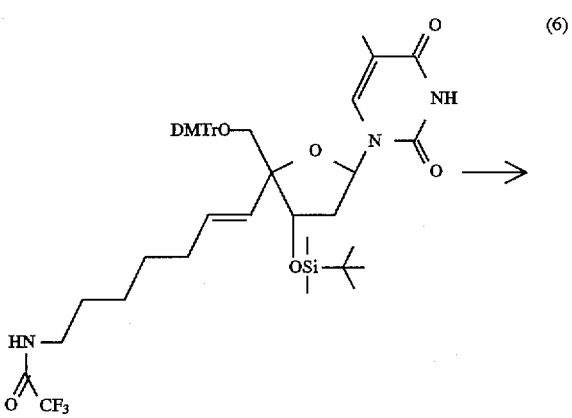

To a solution of Compound (6) (370 mg, 0.42 mmole) in tetrahydrofuran (10 mL) under nitrogen was added tetrabutyl ammonium fluoride (4.3 mL of a 1M solution in THF, 4.3 mmole). The mixture was stirred at room temperature for 20 hours. After the addition of ethyl acetate (90 mL) the mixture was washed with saturated sodium bicarbonate (30 mL) followed by water (30 mL) and brine (30 mL). The aqueous fractions were back extracted with ethyl acetate (50 mL). The combined organic extracts were dried over magnesium sulfate, concentrated under reduced pressure and the crude material was chromatographed on a silica gel column with ethyl acetate/hexane mixtures resulting in 304 mg (95%) of 5'-O- (4,4'-dimethoxytrityl)-4'-(7-trifluoroacetamido-1-hepten-1-yl)-thymidine (7).

I). Synthesis of 3'-O-[2-cyanoethyl bis(isopropyl) phosphoramidite]-5'-O-(4,4'-dimethoxytrityl)-4'-(7-trifluoroacetamido-1-hepten-1-yl)-thymidine (8).

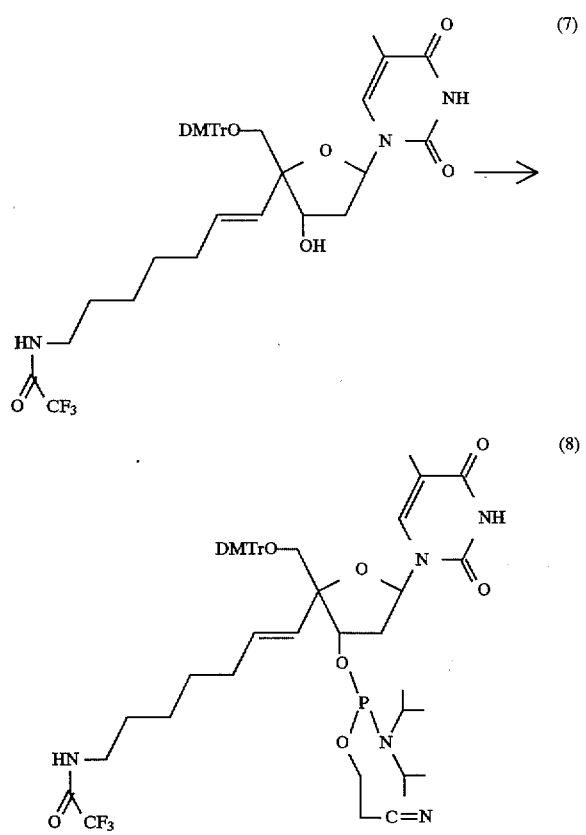

To Compound (7) (300 mg, 0.40 mmole) in dry tetrahydrofuran (11 mL) was added N,N-diisopropylethylamine (1.4 mL, 8 mmole) followed by 2-cyanoethyl bis(isopropyl) chlorophosphoramidite (178 μL, 0.8 mmole). The mixture was stirred at room temperature for 20 hours, diluted with ethyl acetate (100 mL) and washed with a saturated aqueous sodium bicarbonate solution (40 mL). The aqueous phase was again extracted with ethyl acetate (100 mL) and the combined extracts were dried over magnesium sulfate and concentrated under vacuum to a yellow oil. Chromatography on silica gel with ethyl acetate/hexane=1:1 (containing 1% triethylamine) gave 3'-O-[2-cyanoethyl bis(isopropyl) phosphoramidite]-5'-O-(4,4'-dimethoxytrityl)- 4'-(7-trifluroracetamido-1-hepten-1-yl)-thymidine (8) (309 mg, 81%) as a white foam.

EXAMPLE 2

Synthesis of Oligonucleotide Probes

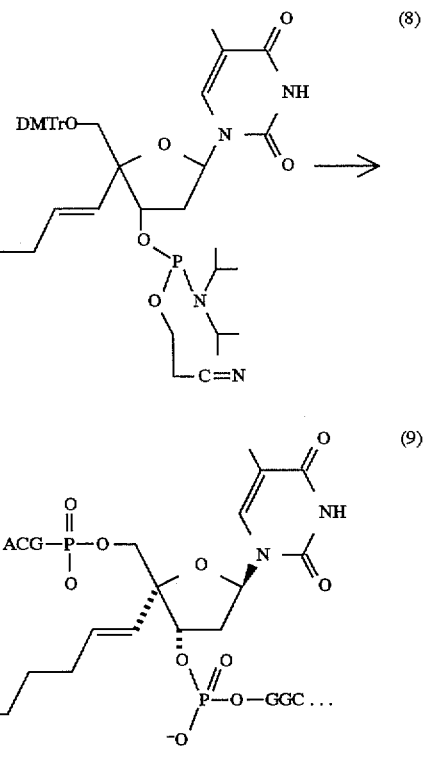

Probes directed at a target sequence in the genome of Mycobacterium tuberculosis (Eisenbach, et al., J. Infect. Disease 16(1):977–981 (1990) were synthesized by the solid phase β-cyanoethyl N,N-diisopropylphosphoramidite method on an automated DNA synthesizer (Milligen/Biosearch 8700). Compound (8) was substituted for the unmodified thymidine reagent at selected positions in three probes. One unmodified probe was synthesized (Probe R) and an oligonucleotide containing the target sequence were also prepared. Coupling efficiencies were monitored by the intensity of the trityl cation color in the trityl deprotection cycle. No difference in the coupling yield between modified or unmodified thymidine monomers was seen. The oligonucleotides were cleaved from the solid support by treatment with ammonium hydroxide, which concomitantly removed the N-trifluoroacetyl protection group at the end of the 4'-chain of the modified thymidines, leaving a 4'-(7-amino-1-hepten-1-yl) substituent. Purification of the crude oligonucleotides was achieved by chromatography through a Oligo-Pak column (Milligen/Biosearch) followed by reverse phase HPLC.

The modified probes were biotinylated at the 4' position with biotinyl-ε-caproic-N-hydroxy succinimide ester utilizing the biotin labeling kit K1016-1 obtained from CLONTECH to provide Probes A, B and C, respectively. Following this procedure, the probes contained a 4'-(7-(biotinyl-ε-caproylamino) hepten-1-yl) substituent on the modified thymidine units (10). The biotinylated probes were purified by Sephadex G-25 column chromatography followed by reverse phase HPLC.

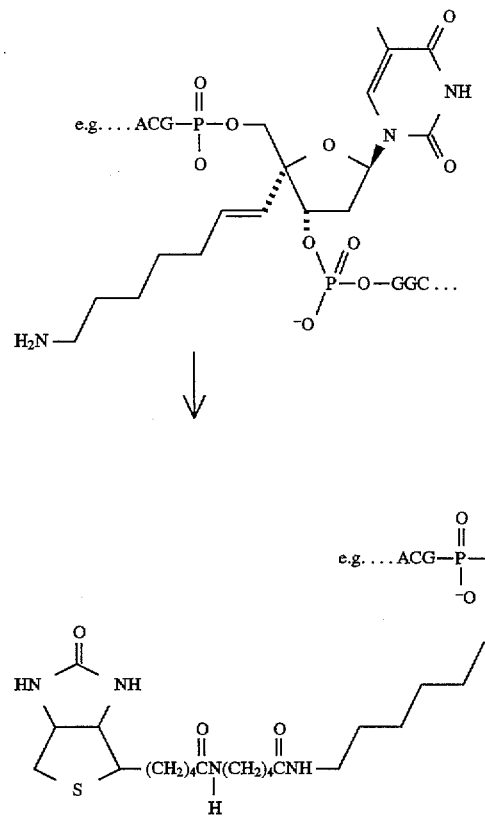

Biotinylation efficiencies were estimated spectrophotometrically as follows: Probe A: 86%, Probe B: 73% and Probe C: 38%. The biotinylated Probes A, B and C are set forth below, where T* denotes a thymidine unit containing a 4'-(7-(biotinyl-ε-caproylamino) hepten-1-yl) substituent. As mentioned above, an unmodified control probe (R) and a oligonucleotide containing the target sequence were also synthesized:

| | |
|---|---|
| Probe A: one 4'-modified nucleotide 5'GTTTCGCCTACGT*GGCCTTTG3' | (SEQ ID NO:1) |
| Probe B: three 4'-modified nucleotides 5'GTT*CGCCTACGT*GGCCTT*TG3' | (SEQ ID NO:2) |
| Probe C: four 4'-modified nucleotides 5'GTT*CGCCT*ACGT*GGCCTT*TG3' | (SEQ ID NO:3) |
| Probe R: unmodified 5'GTTCGCCTACGTGGCCTTTG3' | (SEQ ID NO:4) |
| Target Sequence 5'CAAGCGGATGCACCGGAAAC3' | (SEQ ID NO:5) |

The ability of the modified and unmodified probes to form double stranded DNA molecules with the target sequence was evaluated by determining the melting temperatures of the duplexes. As can be seen from the table below, each additional 4'-modified nucleotide results in a lowering of the melting temperature by approximately 1.5° to 2.0° C., yet these changes are small enough to allow for a selective hybridization by all three probes as shown by DNA dot blot assays. These changes are significantly smaller than the changes observed with other labeling techniques utilized in the art that allow the attachment of the label in the middle of the probe. For example, the covalent attachment of a short linker, -CH$_2$CH$_2$NH$_2$, at the N$_4$-position of a deoxycytidine residue lowers the T$_m$ by 7° C., as disclosed in MacMillan, et al., Tetrahedron 47:2603–2616 (1991).

| Duplex | T$_m$ (°C.) |
|---|---|
| Target Sequence + Probe R | 66.2 |
| Target Sequence + Probe A | 64.5 |
| Target Sequence + Probe B | 62.6 |
| Target Sequence + Probe C | 60.1 |

EXAMPLE 3

Hybridization Assay

DNA dot blot assays were performed with the substituted probes of Example 2 using purified control DNA as well as a PCR amplified fragment from *Mycobacterium tuberculosis* (123 mer) containing the target sequence. A standard protocol for amplifying the DNA was followed.

Aliquots from this reaction were denatured and dot-blotted onto DuPont Gene-Screen Plus filters using standard protocols. Negative (non-target) DNA controls included denatured PCR amplified human DNA, denatured *E. coli* genomic DNA and herring sperm DNA. Triplicate dot blot filters of identical composition were made.

The filters were separately hybridized to one of the modified probes (A, B or C) at a final concentration of 3 nM probe in a standard filter hybridization medium at 49° C. overnight. The three dot blot filters were then pooled and processed according to the Bethesda Research Labs Blu-Gene detection system, which uses a streptavidin/alkaline phosphatase conjugate for detection of the hybridized biotinylated probes.

Dye deposition onto the filter clearly demonstrated specific hybridization of all three probes to the amplified *Mycobacterium tuberculosis* DNA and no detectable hybridization to non-target DNA's.

All three probes easily detected an estimated 2.5 fmoles of target amplicon. Probes B and C detected approximately 0.6 fmole of amplicon. It was further found that there was a distinctively stronger signal with the Probes B and C as compared to Probe A, i.e., Probes B and C were approximately equal in dye intensity on the blot filter and each distinctly more intense than the dye bands from Probe A hybridization. This indicated that multiple biotin labels per nucleotide probe are more easily detected than a single biotin per probe. It appeared however, that Probe B gave a slightly stronger signal than Probe C. This was not unexpected since the labels in Probe C are crowded and not all of the labels may be able to interact with streptavidin.

Although the foregoing invention has been described in some detail by way of illustration and example for the purposes of clarity and understanding, it will be obvious that certain changes or modifications may be practiced within the scope of the appended claims.

What is claimed is:

1. An improved method of detecting the presence or amount of a target nucleic acid in a sample suspected of containing said target nucleic acid, said method comprising the steps of:

(a) providing in combination a medium suspected of containing said target nucleic acid and at least one nucleotide probe capable of binding to a region of said target nucleic acid; and (b) determining whether said nucleotide probe has become bound to said target nucleic acid thereby indicating the presence or amount of said target nucleic acid, the improvement comprising said nucleotide probe having at least one nucleotide that has a substituent other than hydrogen at the 4'-position of the sugar moiety, said substituent being capable of facilitating the detection of said nucleotide probe.

2. The method of claim 1 wherein said substituent renders said nucleotide modifiable, separable or detectable.

3. The method of claim 1 wherein said substituent is selected from the group consisting of detectable labels, specific binding pair members, DNA intercalators, minor groove binders, nucleic acid modifying catalysts and cleavage agents.

4. A method for detecting the presence of a polynucleotide analyte in a sample suspected of containing said polynucleotide analyte, said method comprising the steps of:

(a) providing in combination a medium suspected of containing said polynucleotide analyte and at least one nucleotide probe capable of binding to a region of said polynucleotide analyte, said nucleotide probe having at least one nucleotide that has a substituent other than hydrogen at the 4' position of the sugar moiety, said substituent being capable of facilitating the detection of said nucleotide probe; and (b) determining whether said nucleotide probe has become bound to said polynucleotide analyte thereby indicating the presence of said polynucleotide analyte.

5. The method of claim 4 wherein said polynucleotide analyte is DNA or RNA.

6. The method of claim 5 wherein said DNA is from a virus, bacterium or a fungus.

7. The method of claim 6 wherein said polynucleotide analyte is *Mycobacterium tuberculosis* DNA.

8. The method of claim 4 wherein said substituent facilitates the detection of said nucleotide probe by rendering said nucleotide probe modifiable, separable or detectable.

9. The method of claim 4 wherein said substituent is biotin.

10. The method of claim 4 wherein said nucleotide has the structure:

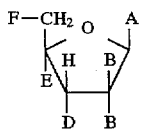

wherein:
- A is a purine or a pyrimidine;
- B and B' are selected from the group consisting of H, OH and F, provided that at least one is H;
- D' is selected from the group consisting of OH and O-P(O)(OH)-OX, where X is selected from the group consisting of H, a nucleotide, and a protecting group;
- E' is RY, where Y is selected from the group consisting of H and a substituent that renders said nucleotide modifiable, separable or detectable and R is a linking group; and
- F is selected from the group consisting of OH and O-P(O)(OH)-OX, where X is selected from the group consisting of H, a nucleotide and a protecting group.

11. The method of claim 10 wherein R is selected from the group consisting of alkylene, alkyl, alkenyl, alkadienyl, aralkyl, aminoalkyl and alkylether.

12. The method of claim 10 wherein Y is biotin.

13. The method of claim 10 wherein Y is a reactive functional group that renders said nucleotide modifiable and is selected from the group consisting of $NH_2$, SH, OH, COOH, $NHC(O)CF_3$ and CHO.

14. The method of claim 10 wherein Y is a substituent that renders said nucleotide modifiable and is selected from the group consisting of nucleic acid modifying catalysts, DNA intercalators, minor groove binders and cleavage agents.

15. The method of claim 14 wherein said DNA intercalator is selected from the group consisting of ethidium, ethidium bromide, acridines, phenazine, phenazinium salts, pyrenes, diazapyrenes, psoralen, psoralen analogs and anthraquinones.

16. The method of claim 14 wherein said nucleic acid modifying catalyst is selected from the group consisting of nucleases, methylases and metal chelates.

17. The method of claim 14 wherein said minor groove binder is selected from the group consisting of distamycin, netropsin and bis-benzimidazoles.

18. The method of claim 14 wherein said cleavage agent is selected from the group consisting of metal complexes and DNA intercalators.

19. The method of claim 10 wherein Y is a specific binding pair member.

20. The method of claim 10 wherein Y is a detectable label.

21. The method of claim 10 wherein said detectable label is selected from the group consisting of enzymes, fluorescers, chemiluminescers, sensitizers, particles and catalysts.

22. The method of claim 10 wherein A is selected from the group consisting of adenine, guanine, xanthine, hypoxanthine, uracil, thymine and cytosine.

23. A kit for the detection of a polynucleotide analyte or target nucleic acid comprising in packaged combination at least one nucleotide probe capable of binding to a region of said analyte or target sequence, wherein said probe has at least one nucleatide that has a substituent other than hydrogen at the 4' position of the sugar moiety so that the probe can be labeled or bound to a support or can be provided with groups to render the probe labeled or bound to a support.

* * * * *